United States Patent [19]

Matula et al.

[11] Patent Number: 5,514,159
[45] Date of Patent: May 7, 1996

[54] GUILLOTINE SUTURE CLIP

[75] Inventors: Paul A. Matula, Brookfield; Douglas J. Cuny, Bethel, both of Conn.

[73] Assignee: United States Surgical Corporation, Norwalk, Conn.

[21] Appl. No.: 305,001

[22] Filed: Sep. 13, 1994

[51] Int. Cl.$^6$ .................................................. A61B 17/04
[52] U.S. Cl. ........................ 606/232; 606/151; 24/115 H; 24/136 R
[58] Field of Search ..................... 606/151, 232; 24/115 H, 115 R, 115 M, 136 R; 289/1.5, 17

[56] References Cited

U.S. PATENT DOCUMENTS

| | | | |
|---|---|---|---|
| D. 190,787 | 6/1961 | Schneider | D24/27 |
| D. 234,204 | 1/1975 | Miller et al. . | |
| 600,887 | 3/1898 | Pettit . | |
| 3,698,681 | 10/1972 | Lacey . | |
| 3,753,438 | 8/1973 | Wood et al. . | |
| 3,803,670 | 4/1974 | Johnson . | |
| 3,854,482 | 12/1974 | Laugherty et al. . | |
| 3,857,396 | 12/1974 | Hardwick . | |
| 3,896,527 | 7/1975 | Miller et al. . | |
| 3,910,281 | 10/1975 | Kletschka et al. | 606/252 |
| 3,976,079 | 8/1976 | Samuels et al. . | |
| 4,291,698 | 9/1981 | Fuchs et al. | 606/232 |
| 4,382,453 | 5/1983 | Bujan et al. . | |
| 4,387,489 | 6/1983 | Dudek . | |
| 4,470,737 | 9/1984 | Wollar . | |
| 4,492,232 | 1/1985 | Green . | |
| 4,498,476 | 2/1985 | Cerwin et al. . | |
| 4,519,392 | 5/1985 | Lingua . | |
| 4,536,924 | 8/1985 | Willoughby . | |
| 4,556,058 | 12/1985 | Green . | |
| 4,557,263 | 12/1985 | Green . | |
| 4,569,346 | 2/1986 | Poirier . | |
| 4,579,473 | 4/1986 | Brugger . | |
| 4,620,541 | 11/1986 | Gertzman et al. . | |
| 4,623,102 | 11/1986 | Hough, Jr. | 606/232 |
| 4,750,492 | 6/1988 | Jacobs | 606/232 |
| 4,866,818 | 9/1989 | Thompson | 24/543 |
| 4,969,892 | 11/1990 | Burton et al. | 606/218 |
| 5,078,731 | 1/1992 | Hayhurst | 606/232 |
| 5,143,500 | 9/1992 | Schuring et al. | 411/339 |
| 5,160,339 | 11/1992 | Chen et al. | 606/158 |
| 5,171,251 | 12/1992 | Bregen et al. | 606/151 |
| 5,282,832 | 2/1994 | Toso et al. | 606/232 |
| 5,391,173 | 2/1995 | Wilk . | |

FOREIGN PATENT DOCUMENTS

| | | |
|---|---|---|
| 0634142 | 6/1994 | European Pat. Off. . |
| 0635241 | 6/1994 | European Pat. Off. . |

OTHER PUBLICATIONS

"A Technique For Suturing Soft Viscera Using Compression Sutures", O. Drew Grice, M.D. F.A.C.S., Surgery, Gynecology & Obstetrics, vol. 167, pp. 523–524 (Dec., 1988).
"Absorbable Ligating Clips", Schaefer et al., Surgery, Gynecology & Obstetrics, vol. 154, pp. 513–516 (Apr. 1982).

*Primary Examiner*—Gary Jackson

[57] ABSTRACT

A suture retainer includes a plug portion having a first portion with a suture contacting surface and a prong extending distally therefrom. The prong has at least one aperture for receiving one or more suture threads. The aperture is at least partially defined by a crossbar with a proximal stop surface. The crossbar preferably includes a beveled distal edge. The suture retainer also includes a receptacle portion having a slot for receiving a prong. The receptacle portion has a resilient latch positioned inside the slot for preventing proximal withdrawal of the first portion. The latch being a resilient member projecting from the inner wall of the receptacle slot and including an inclined proximal surface and a distal blocking surface for engaging the proximal stop surface of the crossbar. The suture retainer may optionally be fabricated from a bioabsorbable synthetic resin.

10 Claims, 2 Drawing Sheets

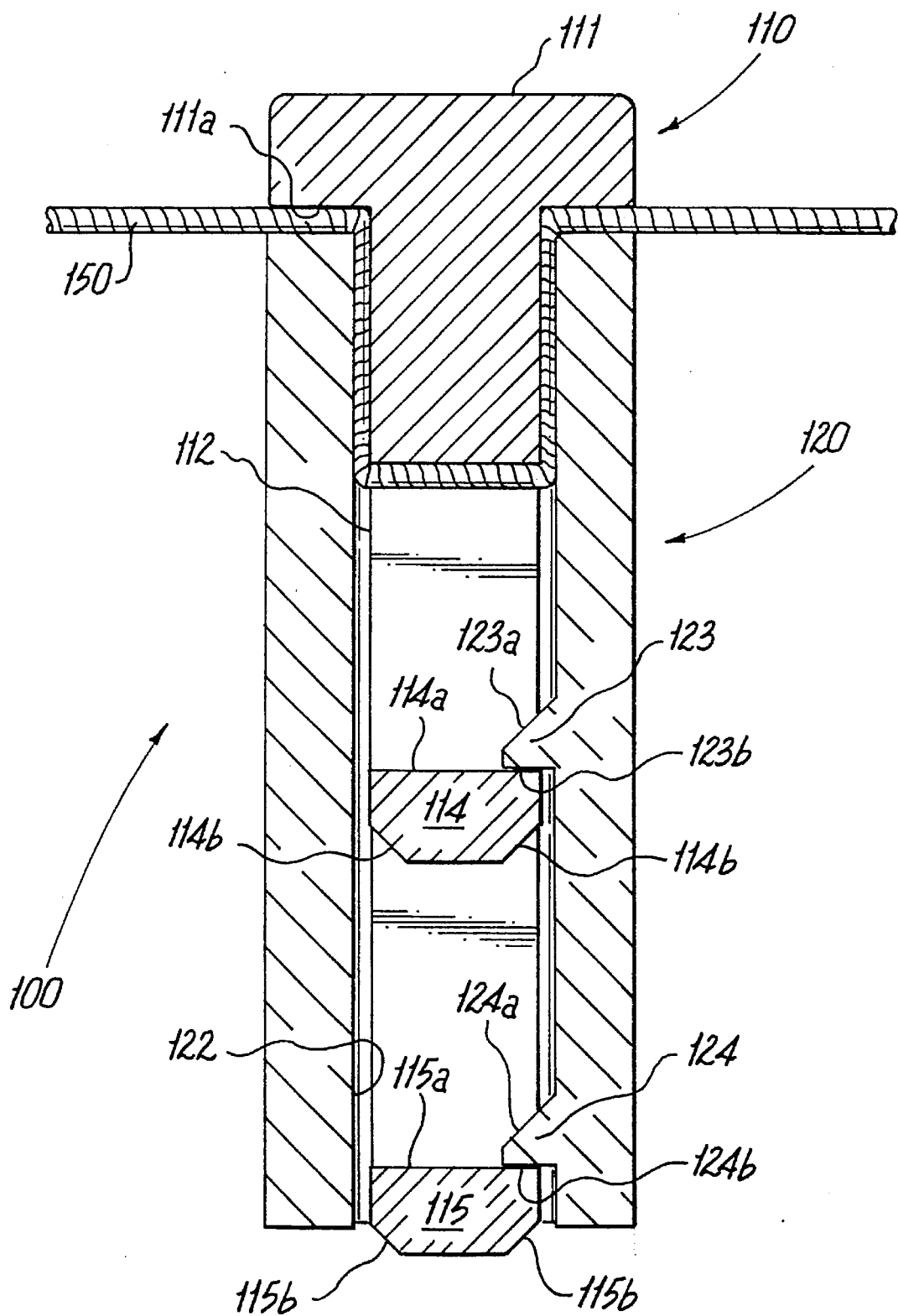

GUILLOTINE SUTURE CLIP

BACKGROUND OF THE INVENTION

1. Field of the Invention

The present invention relates to a fastening device for use in surgical procedures to secure a suture.

2. Background of the Art

Sutures are commonly used to close incisions and to reunite damaged tissue. Typically, the sutures are passed through the tissue and the free ends of the sutures are tied together. In many instances, the suturing site is exposed to an extent sufficient to permit the surgeon to quickly tie the suture by hand. However, in some procedures such as arthroscopic, laparoscopic or endoscopic surgery, the suturing site is inaccessible by hand. As a result, the surgeon is usually required to tie the suture ends into a knot at a location remote from the suture site, and then manipulate suitably configured instruments for sliding the knot to the site.

For example, arthroscopic surgical procedures usually employ a small diameter cannula that extends through a small incision made in a joint. The sutures extend from the suturing site through the cannula. The exposed free ends of the sutures are tied by the surgeon and the knot is slid through the cannula to the suturing site.

Likewise, laparoscopic or endoscopic surgery also relies on small diameter cannulas to insert through small incisions in body tissue to gain access to the interior of the body. The operating instruments have relatively long and narrow portions which are inserted through a cannula to perform the operation in the interior of the body. The instrumentation for such procedures is actuated from outside the body. It can readily be understood that the dexterity required to free suture ends under such conditions not only places a burden upon the operating personnel, but also poses a greater risk to the patient.

Various devices are known which attempt to deal with the aforementioned problem.

U.S. Pat. No. 5,282,832 to Toso et al., herein incorporated by reference, discloses a suture clip which comprises a two piece structure, the members of which engage to hold a suture therebetween in a serpentine fashion.

For example, U.S. Pat. No. 5,078,731 to Hayhurst discloses a suture clip for engaging one or more suture thread lines. The Hayhurst suture clip, in an open position, is slidable along the suture(s). When positioned at the suturing site, the Hayhurst clip may then be closed to fix the position of the clip, thereby securing the suture(s).

U.S. Pat. No. 4,291,698 to Fuchs et al. discloses a button type suture retainer including a disk having a slot which extends to a passage for guiding a suture thread therethrough within the circumference of the disk. The passage is sealed by a clamping device for clamping a thread in the passage. The clamping device includes a disk segment movable parallel with the disk over the slot and passage to a latched position where its inner marginal part is past the passage, thereby bending the thread and holding it by friction and compression.

Other suture fixation devices are disclosed in U.S. Pat. Nos. 3,753,438; 3,857,396; 3,910,281; 3,976,079; 4,387,489; 4,750,492; and 4,969,892.

While the aforementioned devices perform the function of suture retention, there is yet need for an improved suture retainer clip which is simple in construction, easy to apply, and usable in laparoscopic or endoscopic or arthroscopic applications as well as in conventional surgical procedures.

SUMMARY OF THE INVENTION

A suture retainer is provided herein for holding a suture in a serpentine fashion. The suture retainer comprises a plug portion including a first portion having a suture contacting surface and a prong extending distally, and preferably perpendicularly, from the suture contacting surface. The prong has at least one aperture for receiving one or more suture threads. The aperture is at least partially defined by a crossbar with a proximal stop surface. The crossbar preferably includes a beveled distal edge.

The suture retainer also comprises a receptacle portion having a slot for receiving the prong. The receptacle portion has resilient latch means positioned inside the slot for preventing proximal withdrawal of the first portion. The latch means preferably comprises a resilient member projecting from the inner wall of the receptacle slot, the resilient member including an inclined proximal surface and a distal blocking surface for engaging the proximal stop surface of the crossbar.

The suture retainer may optionally be fabricated from a bioabsorbable synthetic resin.

BRIEF DESCRIPTION OF THE DRAWINGS

FIG. 3 is a sectional side elevational view of the suture retainer in conjunction with a suture.

DETAILED DESCRIPTION OF PREFERRED EMBODIMENT(S)

Figure 1:
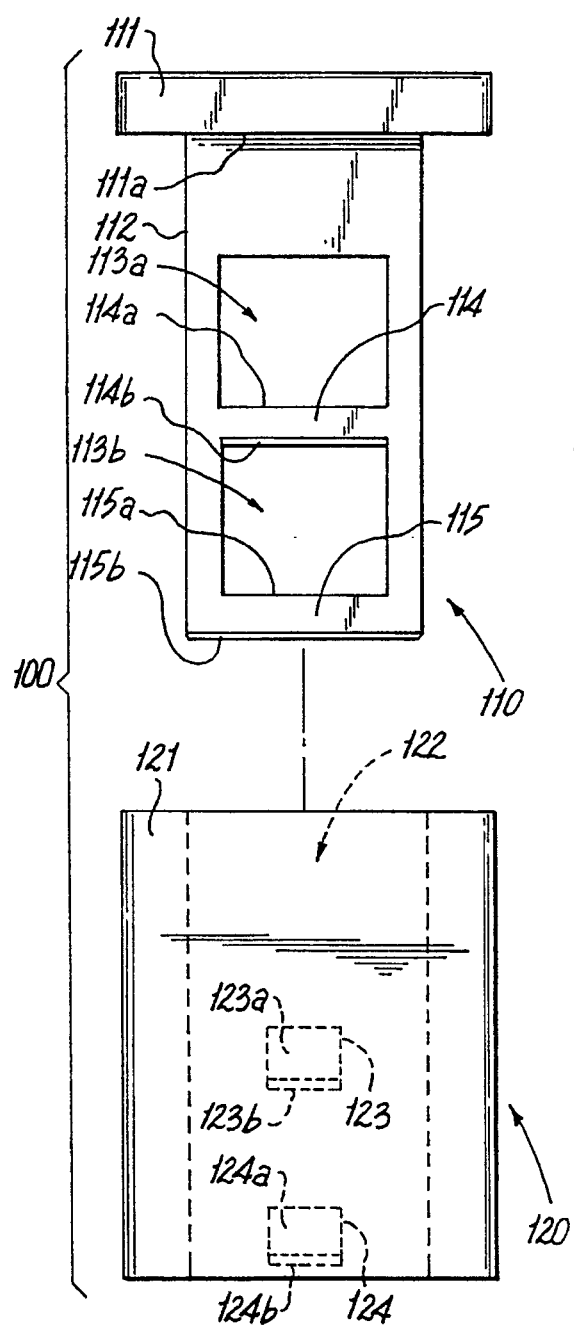
FIG. 1 is an exploded front elevational view of the suture retainer of the present invention.
Figure 2:
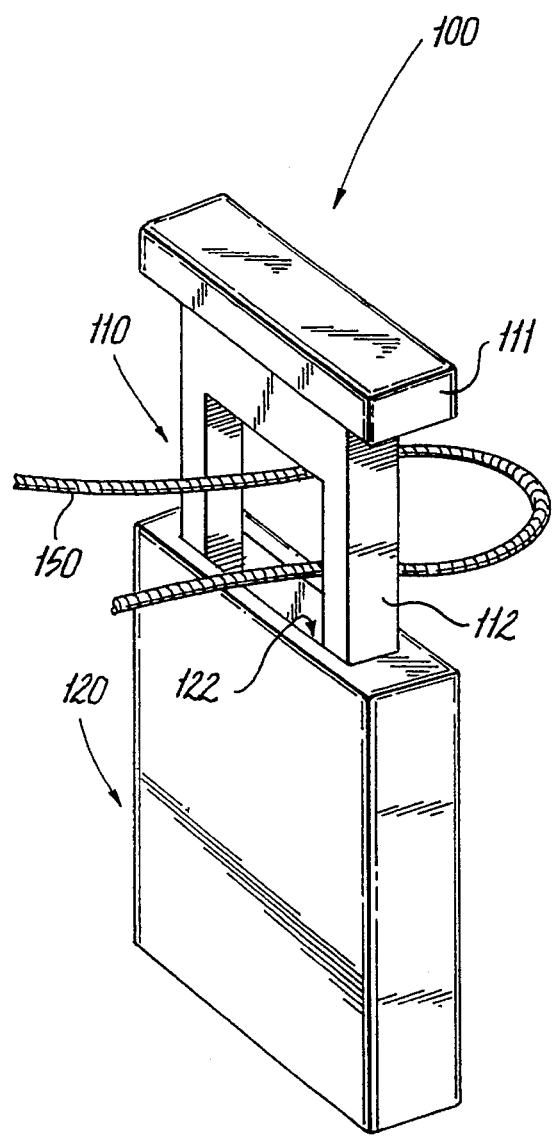
FIG. 2 is a perspective view of the suture retainer in conjunction with a suture.

Referring to FIGS. 1, 2, and 3, the suture retainer 100 of the present invention comprises a plug portion 110 and a receptacle portion 120. The plug portion 110 includes a generally rectangular top member 111 which has a suture contacting under surface 111a. Projecting downwardly (as shown in the drawings) from the suture contacting surface 111a is a rectangular prong member 112 which is insertable into a slot 122 in the receptacle 120. Slot 122 may be rectangular or oval in cross-section. The prong 112 includes at least one, and preferably two, window-like apertures 113a and 113b for receiving a suture thread therethrough. The apertures 113a and 113b are at least partially defined by crossbars 114 and 115. The top surface of each crossbar, i.e. surfaces 114a and 115a, respectively, provide a stop surface for engagement with a latching mechanism (described below) to prevent withdrawal of the plug portion 110 from the receptacle portion 120 after the prong 112 has been inserted into the receptacle portion 120. The crossbars 114 and 115 may optionally include a beveled under edge 114b and 115b, respectively, to facilitate insertion of the prong.

The receptacle portion 120 is a generally rectangular member having a slot 122 extending longitudinally therethrough for receiving prong 112 of the plug portion. The receptacle 120 further includes latching members 123 and 124 positioned in the inner wall of the slot 122 such that when the prong 112 is fully inserted latch 123 engages crossbar 114 and latch 124 engages crossbar 115.

Each latch 123 and 124 includes an upper inclined upper surface (123a and 124a, respectively), and a lower surface (123b and 124b, respectively) which is oriented at a right angle to the longitudinal orientation of the slot 122.

During insertion the beveled edges 114b and 115b contact and cam against the inclined upper surfaces 123a and 124a. Because of the resiliency of the latches 123 and 124, and the relatively loose tolerance between the walls of the prong 112 and the inner walls of the slot 122, latches 123 and 124 bend sufficiently to permit the crossbars 114 and 115 to pass the latches during insertion. When prong 112 is fully inserted, the lower surfaces 123b and 124b engage the upper stop surfaces 114a and 115a, respectively, of the crossbars to prevent withdrawal of the prong 112 form slot 122.

The plug portion 110 and the receptacle portion 120 may be individually fabricated as single pieces and are preferably molded from a bioabsorbable synthetic resin such as homopolymers and copolymers of glycolide, lactide, p-dioxanone, caprolactone, trimethylene carbonate, and blends thereof. Non-bioabsorbable polymers may also be used, as well as metals such as stainless steel and titanium.

Suture retainer 100 may be employed in open surgical procedures and applied by hand. Alternatively, when appropriately configured and dimensioned, suture retainer 100 may be used in minimally invasive surgical procedures, such as laparoscopic, endoscopic, or arthroscopic surgery. For minimally invasive procedures, the suture retainer should be of such size as to be insertable through a trocar cannula. Generally, trocar cannulas range in size from about 8 mm to 12 mm in diameter. Conventional laparoscopic/endoscopic manipulating and clamping devices can be used to position and apply the suture retainer 100.

In use during a surgical procedure, the surgeon inserts a suture through one or both of apertures 113a and 113b. The prong is then inserted into slot 122 until the latches are engaged. Engagement of the latches is indicated tactually as the crossbars encounter resistance when camming against the latches, followed by decreased resistance as the latch is passed. The suture 150 is frictionally held in serpentine fashion between suture contacting surfaces of the plug portion 110 and receptacle portion 120.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed:

1. A suture retainer, which comprises:
    a) a plug including a first portion having a suture contacting surface and a prong extending distally from said suture contacting surface, said prong having at least two apertures for receiving a suture thread, said apertures being at least partially defined by a crossbar spaced distal from said contacting surface with a proximal stop surface;
    b) a receptacle portion having a slot for receiving said prong, said receptacle portion having resilient latch means positioned inside said slot for preventing proximal withdrawal of said first portion.

2. The suture retainer of claim 1, wherein said prong is oriented substantially perpendicularly to said suture contacting surface.

3. The suture retainer of claim 2 wherein said prong is substantially rectangular in shape.

4. The suture retainer of claim 1 wherein said at least two apertures of said prong are substantially rectangular in shape.

5. The suture retainer of claim 1 wherein said crossbar has a beveled distal edge.

6. The suture retainer of claim 1 wherein said receptacle slot is rectangular in shape.

7. The suture retainer of claim 1 wherein said latch means comprises a resilient member projecting from an inner wall of said receptacle slot, said resilient member including an inclined proximal surface and a distal blocking surface for engaging said proximal stop surface of said crossbar.

8. The suture retainer of claim 1 wherein said suture retainer is fabricated from a synthetic bioabsorbable resin.

9. The suture retainer of claim 8 wherein said synthetic bioabsorbable resin is a material selected from the group consisting of polymers of lactide, glycolide, caprolactone, p-dioxanone, trimethylene carbonate, and chemical and physical combinations thereof.

10. In combination with the suture retainer of claim 1, a suture, wherein said suture is held in said suture retainer in a serpentine fashion.

* * * * *